Figure 1:
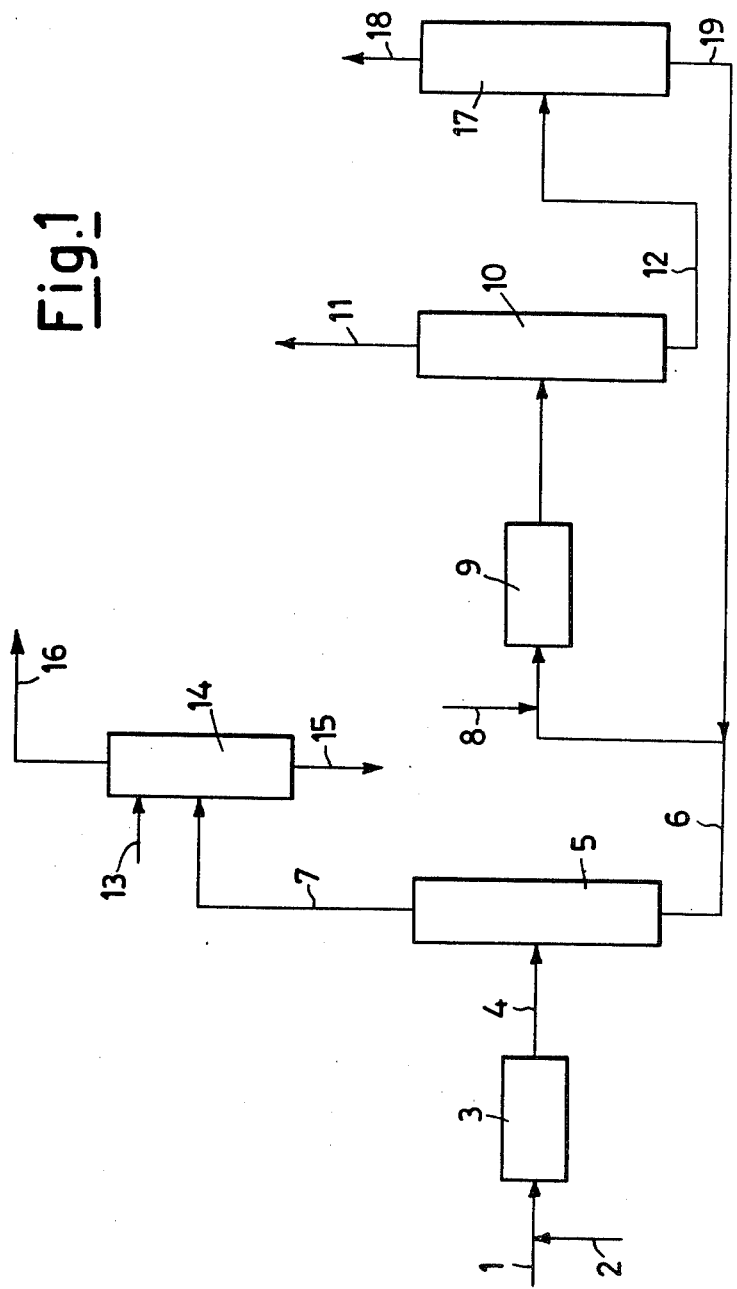

United States Patent [19]

Rescalli et al.

[11] 4,132,739
[45] Jan. 2, 1979

[54] METHOD FOR THE PREPARATION OF CARBONYL PRODUCTS STARTING FROM HYDROCARBON STREAMS COMING FROM STEAM-CRACKING INSTALLATIONS

[75] Inventors: Carlo Rescalli; Antonio Pacifico, both of San Donato Milanese (Milan), Italy

[73] Assignee: Snam Progetti S.p.A., Milan, Italy

[21] Appl. No.: 702,584

[22] Filed: Jul. 6, 1976

[30] Foreign Application Priority Data

Jul. 8, 1975 [IT] Italy .................... 25169 A/75

[51] Int. Cl.² ........................................... C07C 45/06
[52] U.S. Cl. .............................. 260/605 S; 260/593 R
[58] Field of Search ........... 260/605 R, 605 S, 593 R, 260/597

[56] References Cited

U.S. PATENT DOCUMENTS 2,853,520  9/1958  Newman .................... 260/605 S

Primary Examiner—James O. Thomas, Jr.
Assistant Examiner—Werren B. Lone
Attorney, Agent, or Firm—Morgan, Finnegan, Pine, Foley & Lee

[57] ABSTRACT

A method is disclosed for preparing carbonyl compounds from hydrocarbon streams coming from steam-cracking installations, the improvement consisting in that an alcohol is added to such a stream in a first reaction area and in the presence of an acidic ion-exchange resin the acidic centers of which have totally been exchanged with mercuric ions and with ions of alkali metals or alkaline earth metals, the resultant product being rectified to separate it from the hydrocarbon stream and then hydrolyzed in a second reaction area in the presence of an acidic ion-exchange resin and finally recovered by rectification.

7 Claims, 1 Drawing Figure

METHOD FOR THE PREPARATION OF CARBONYL PRODUCTS STARTING FROM HYDROCARBON STREAMS COMING FROM STEAM-CRACKING INSTALLATIONS

This invention relates to a method for the preparation of carbonyl products starting from hydrocarbon streams coming from steam cracking installations.

More particularly, the present invention relates to a method for the preparation of carbonyl products by exploiting the acetylenic compounds as contained in the hydrocarbon streams coming from steam-cracking.

Still more detailedly, the present invention relates to a method for the preparation of:

1. acetaldehyde by utilizing the acetylene which is contained in the $C_2$-stream coming from steam-cracking.
2. acetene by utilizing the propyne as contained in the $C_3$-stream coming from steam cracking.

The amounts of acetylene ($C_2\equiv$) and propyne ($C_3\equiv$) in the $C_2$-stream (ethylene, ethane, acetylene) and in the $C_3$-stream (propylene, propane, propyne) are widely variable according to the run conditions of the steam-cracking (type of charge working temperature, and others). As a conservative estimate it can be said that, as an average, the production of the two acetylenic compounds aforementioned is about the 4% of the asproduced ethylene, so that it can be estimated to have available about 20,000 metric tons a year of $C_2\equiv$ + $C_3\equiv$ from a conventional installation for the production of ethylene (500,000 metric tons a year output).

On the other hand, acetylene and propyne involve not negligible purification problems in the recovery of ethylene and propylene, inasmuch as the levels of the same acetylenic compounds must be usually reduced to a few tens of parts per million and even less in the above mentioned olefin stream.

At present, such a reduction is carried out by selective hydrogenation, which involves losses of ethylene and propylene which are more or less important consistently with the level of acetylenic compounds which is present on completion of the operation.

It has been surprisingly found that it is possible to recover the acetylenic compounds which are contained in streams as obtained from steam-cracking in the form of carbonyls, and thus without resorting to their selective hydrogenation to purify said streams as obtained from steam-cracking.

An object of the present invention is to provide a method for the preparation of carbonyl products starting from hydrocarbon streams coming from steam-cracking installations.

Other and further objects of the present invention will become apparent from the ensuing description.

The method which is the subject-matter of the present invention comprises the steps of:

1. adding to the acetylenic compounds, in a first reaction zone, an alcohol, more particularly methanol, or ethanol, in the presence of an ion-exchange resin of acidic type the active centres of which have totally been exchanged with mercury ions ($Hg^{++}$) and with ions of alkali metals or alkaline earth metals ($Me^{n+}$).
2. separating the vinyl ether and/or the gem-diether which have been formed, by a rectification operation of the remainder of the hydrocarbon stream.
3. hydrolyzing the thusly obtained vinylether and/or gem-diether, in the presence of an acidic ion-exchange resin in a second reactor.
4. separating the as obtained carbonyl product by a rectification operation.

With reference to the accompanying drawing, a particular embodiment of the method of the present invention will now be described.

Said embodiment has the following provisions:

the hydrocarbon stream (1) (cutting $C_2$ or $C_3$) is sent together with a stream of alcohol (2) into the reactor (3), the stream emerging from the reactor (4) is subjected to a simple rectification at (5) so as to remove the asformed addition product as a tail fraction (6), whereas the hydrocarbons, and possibly the unreacted alcohol are dumped from the head (7).

the stream (6) is supplemented with water (8) whereafter the whole is sent to the hydrolysis ractor (9);

the product emerging from (9) is sent to the rectification column (10), from the head of which (11) the carbonyl product (acetaldehyde or acetone according to the cutting which had been fed to the process) is recovered, whereas the excess water which had been sent to the hydrolysis reactor is dumped through the bottom (12). This stream also contains the alcohol as a result of the hydrolysis.

the hydrocarbon stream (7) is sent to a gas-liquid scrubber column (14) for removing the unreacted alcohol which is possibly present in it (to this purpose, water fed through the main 13 is used);

the hydrocarbon stream (16) emerging from 14 is sent to the subsequent purification stages as provided for the hydrocarbon cutting concerned (for example separation of olephins from saturated compounds). The stream (15), substantially composed by water and alcohol, can possibly be sent to the column (17) to recover the alcohol as contained therein;

the stream (12) is sent to the rectification clumn (17) 8). from the head of which alcohol (18) is recovered, which has been used in the addition reaction (recycle towards the line 2), whereas water is dumped (recycle towards 8 ).

In both the reactors, the acidic ion-exchange resin as used, can be selected as any of those available on the market, but it is preferred that a resin which contains sulfonic groups (—$SO_3H$) or carboxyl groups (—$COOH$) be used.

Still more particularly, the support for the resin can be of a polystrene, phenolic or acrylic nature.

The mercuric ions and the ions of the alkali, or alkaline earth-metals (more particularly Na, K, Li, Ca, Ba, Sr) can be added to the resin as used in the first reactor (etherification) in the form of salts; the ions of the alkali metal or of the alkaline earth metals can also be added in the form of hydroxides. The contents of $Hg^{++}$ ions in the same resin can be less than that of the $Me^{n+}$ ions. More particularly, it is peferred that the $Me^{n+}$ ions be added first, and then the ions $Hg^{++}$ and it is also preferred that during the operations aqueous solutions only be used and that the resin be subsequently dehydrated by washing it with methanol, ethanol, or, in general, with the alcohol which is subsequently to be used in the reaction.

The addition reaction can be carried out within a wide range of temperatures and pressures. To work between −20° C and 80° C is an advantage, and still more advantageous is to work between 10° C and 50° C under a pressure selected in such a way as to maintain, at the reaction temperature, in liquid or gaseous phase the hydrocarbon streams concerned (according to the advisability of treating said streams in the liquid or the vapor phase).

By operating in the liquid phase, the spatial velocity (LHSV) of the reaction is comprised between 1 and 50 (cc/h.g). It is advisable to work in the presence of a stoichiometric excess of the alcohol over the acetylenic compound and it is advisable in practice to work with an alcohol to acetylene compound molar ratio of 2.1.

The resin used in the second reactor (hydration) is simply activated prior to being used, with acidic aqueous solutions, generally acetic acid solutions.

Hydration can be carried out within a wide range of temperatures and pressures : to work between 0° C and 100° C is an advantage, and still more advantageous is to work between 20° C and 80° C, under a pressure to be selected in such a way as to maintain, at the reaction temperature, the stream concerned preferably in the liquid condition. By operating in the liquid phase, the spatial velocity (LHSV) of the reaction is comprised between 0.5 and 20 (cc/h.g). It is advisable to work in the presence of an excess of water. In practice, it is advisable to work with a water to ether molar ratio of 2 or over.

An example will now be given, aiming at better illustrating the invention without limiting it in any way.

EXAMPLE

The resin to be used in the reactor in which the addition of the alcohol is carried out, is prepared in the following manner.

98 grams of an acidic resin of the Amberlyst-15 type, containing acidic groups of the type —$SO_3H$, are treated with 2 liters of a 10% aqueous solution ( by weight ) of NaOH. The mixture is stirred during one hour and then filtered and the resin is washed with distilled water until a neutral reaction is obtained. The resin is subsequently treated with 300 mls of an aqueous solution, which is acidified with acetic acid, which contains 2 grams of $Hg^{++}$ (such as mercury acetate), is stirred during 24 hours, then filtered in a vacuum and repeatedly washed with anhydrous ethanol.

The resin to be used in the second reactor is prepared as follows:

100 grams of acidic Amberlyst-15 resin are treated with 2 liters of a 10% aqueous solution of $H_2SO_4$, the solution being kept stirred during one hour, then filtered and the resin is washed with distilled water to neutrality.

Having reference to the accompanying FIG. 1, the reactor (3) (100 mls volume, charged with the resin supplemented with $Hg^{++}$ and $Na^+$ ions) is continuously fed, through the line 1, with 500 mls of a stream of propylene, containing 1.33% by weight of propyne, and ethanol in such an amount as to have an alcohol to acetylenic compound mole to mole ratio of 2.1. The reactor is maintained at 40° C by an appropriate thermostatic circuit and under a pressure of 20 atmospheres.

The stream (4) emerging from the reactor is sent to the rectification column (5) which is operated at a pressure (head) of 10 ata. has an L/D ratio of 1 and contains 30 plates.

While the head stream (7), which is composed by propylene which contains small amounts of ethanol and has a propyne contents of 10 parts per million or less, is sent to the scrubber column with water (14) to remove ethanol, the bottom stream (6) which is formed by 2,2-dimethoxypropane is sent to the hydrolysis reactor (9) after having been supplemented with water (19), the reaction being carried out with a water to ether ratio of 10 mol/ mol. The liquid-liquid scrubber column (14) is operated at a pressure, P, of 20 ata, and with a ratio of water to the hydrocarbon stream of about 1/30 gram/gram. From the head (line 16) there is recovered, virtually ethanol-free (equal to or less than 10 parts per million), all of the propylene which had been fed from 1, whereas there is discharged from the bottom (line 15) an aqueous solution of ethanol. The hydrolysis reactor (9) is operated at 70° C and under a pressure, P, of 20 ata.

The stream emerging from the same reactor is sent to two conventional rectification columns (10) and (17) which are operated under the following conditions:

|  | Column 10 | Column 17 |
|---|---|---|
| Pressure at the head | atmospherical | atmospherical |
| L/D (reflux ratio) | 10 | 5 |
| Number of plates | 40 | 50 |

From the head of the first line (11) there are discharged about 5.8 grams an hour of acetone, whereas from the head of the second line (18) there are discharged 9.7 grams an hour of ethanol (which contains less than 5% by weight of water); the stream (19) as discharged from the bottom and essentially composed by water is recycled to the etherification reactor (9).

What we claim is:

1. A method for the preparation of acetaldehyde and acetone starting from acetylenic compounds contained in the olefin hydrocarbon streams coming from steam-cracking installations, characterized in that the acetylenic compounds are combined with an alcohol in a first reaction zone and in the presence of an acidic ion-exchange resin the acidic centres of which have been entirely exchanged with mercury ions and with ions of alkali metals or alkaline earth metals, separating the reaction product by a rectification operation from the remainder of the olefin hydrocarbon stream and subsequently hydrolyzing said product to acetaldehyde and acetone in a second reactor in the presence of an acidic ion-exchange resin, and thereafter separating the carbonyl product thus obtained by a rectification operation, wherein the first reaction zone the temperature is between −20° C and 80° C, the pressure is sufficient to maintain the olefin hydrocarbon stream in a liquid phase and the spatial velocity is between 1 and 50 cc/h.g; and in the second reactor the temperature is between 0° C and 100° C the pressure is sufficient to maintain the reaction mixture in a liquid phase; and the spatial velocity is between 0.5 and 20 cc/h.g.

2. A method according to claim 1, wherein the acetylenic compound is propyne and the olefin hydrocarbon stream coming from the steam-cracking installation is the $C_3$-stream which comprises propylene, propane, propyne.

3. A method according to claim 1, wherein the acetylenic compound is acetylene and the olefin hydrocarbon stream coming from a steam-cracking installation is the $C_2$-stream which comprises ethylene, ethane, acetylene.

4. A method according to claim 1, wherein the alcohol is selected from methanol and ethanol.

5. A method according to claim 1, wherein the alkali metal or the alkaline earth metal is selected from Na, K, Li, Ca, Ba and Sr.

6. A method according to claim 5 wherein the mole ratio of alcohol to acetylene compound is 2:1.

7. A method according to claim 6 wherein the alkali metal is sodium.

* * * * *